US008426386B2

(12) United States Patent
Uozumi et al.

(10) Patent No.: US 8,426,386 B2
(45) Date of Patent: Apr. 23, 2013

(54) NK1 RECEPTOR ANTAGONIST COMPOSITION

(75) Inventors: Takuya Uozumi, Tokyo (JP); Satoru Morishita, Tokyo (JP); Yoshimasa Tanaka, Tokyo (JP); Mayumi Yumoto, Tokyo (JP)

(73) Assignee: Lion Corporation, Tokyo (JP)

( * ) Notice: Subject to any disclaimer, the term of this patent is extended or adjusted under 35 U.S.C. 154(b) by 391 days.

(21) Appl. No.: 12/445,811

(22) PCT Filed: Oct. 12, 2007

(86) PCT No.: PCT/JP2007/069959
§ 371 (c)(1),
(2), (4) Date: Apr. 16, 2009

(87) PCT Pub. No.: WO2008/047709
PCT Pub. Date: Apr. 24, 2008

(65) Prior Publication Data
US 2011/0039801 A1   Feb. 17, 2011

(30) Foreign Application Priority Data

Oct. 16, 2006   (JP) ................ 2006-281907

(51) Int. Cl.
*A01N 43/04* (2006.01)
*A61K 31/715* (2006.01)

(52) U.S. Cl.
USPC ............................. 514/61; 514/54

(58) Field of Classification Search ........... 514/61, 514/54; 536/123.1
See application file for complete search history.

(56) References Cited

U.S. PATENT DOCUMENTS

| | | | |
|---|---|---|---|
| 5,972,905 A | 10/1999 | Hosokawa et al. | |
| 6,203,803 B1 | 3/2001 | De La Charriere et al. | |
| 6,235,291 B1 | 5/2001 | De La Charriere et al. | |
| 6,333,042 B1 | 12/2001 | De La Charriere et al. | |
| 6,348,201 B2 * | 2/2002 | Murata et al. ............. | 424/401 |
| 2001/0014342 A1 | 8/2001 | De La Charriere et al. | |
| 2005/0265944 A1 | 12/2005 | Cowden | |

FOREIGN PATENT DOCUMENTS

| | | |
|---|---|---|
| EP | 0 834 317 A1 | 4/1998 |
| JP | 1 117831 | 5/1989 |
| JP | 2 229103 | 9/1990 |
| JP | 4-360820 | 12/1992 |
| JP | 5 294837 | 11/1993 |
| JP | 6-219935 * | 8/1994 |
| JP | 7 304649 | 11/1995 |
| JP | 8 208505 | 8/1996 |
| JP | 8 208506 | 8/1996 |
| JP | 8 208508 | 8/1996 |
| JP | 8-217695 * | 8/1996 |
| JP | 3078214 | 8/2000 |
| JP | 2001 81041 | 3/2001 |
| JP | 2001-213772 | 8/2001 |
| JP | 2002 521421 | 7/2002 |
| JP | 2002 308783 | 10/2002 |
| JP | 2003-012501 | 1/2003 |
| JP | 2003 113019 | 4/2003 |
| JP | 2004 161718 | 6/2004 |
| JP | 2005 527498 | 9/2005 |
| JP | 2006 89499 | 4/2006 |
| WO | 97 00075 | 1/1997 |
| WO | WO 03/068243 A1 | 8/2003 |

OTHER PUBLICATIONS

Gove et al., Webster's Third New International Dictionary, 1963, p. 1798.*
Huang et al., Expert Opinion in Ther. Patents, 2010, 20(8), 1019-1045.*
"Itching", Merck Manual Online Edition, [retrieved on Jun. 7, 2011]. Retrieved from the Internet http://www.merckmanuals.com/home/print/sec18/ch203/ch203b.html. Revision Dec. 2006. 14 pages.*
Endo et al., machine translation of JP 8-217695, retrieved from the internet <http://dossier1.ipdl.inpit.go.jp> on Jan. 5, 2011, 9 pages.*
Hikima, T., machine translation of JP 6-219935, retrieved from the internet <http://dossier1.ipdl.inpit.go.jp> on Jan. 9, 2011, 7 pages.*
Miyamoto et al., Jpn. J. Phamacol. 2002, 88, 285-292.*
Yoshino, K. et al., "Preventive Effects Oligosaccharides on Mouse Contact Hypersensitivity", J. Technology and Education, vol. 11, No. 1, pp. 37-41 (2004).
Takayanagi, K., "Cell Membrane Receptor", Nanzando, pp. 255-269 (1998) (with partial English translation).
Kramer, M. S. et al., "Distinct Mechanism for Antidepressant Activity by Blockade of Central Substance P Receptors", Science, vol. 281, pp. 1640-1645 (1998).
Gesztesi, Z. et al., "Substance P (Neurokinin-1) Antagonist Prevents Postoperative Vomiting After Abdominal Hysterectomy Procedures", Anesthesiology, vol. 93, No. 4, pp. 931-937 (2000).
Zubrzycka, M. et al., "Comparison of Antagonistic Properties of Substance P Analogs, Spantide I, II and III on Evoked Tongue Jerks in Rats", Endocrine Regulations, vol. 33, No. 1, pp. 13-18 (2000).
Rost, K. et al., "Neurokinine-1 Receptor Antagonists", Med Monatsschr Pharm, vol. 29, No. 6, pp. 200-205 (2006) (with partial English translation).
Chinese Office Action issued Jul. 20, 2011, in Patent Application No. 200780038468.8 (with English-language translation).

(Continued)

*Primary Examiner* — Eric S Olson
*Assistant Examiner* — Zhengfu Wang
(74) *Attorney, Agent, or Firm* — Oblon, Spivak, McClelland, Maier & Neustadt, L.L.P.

(57) ABSTRACT

An NK1 receptor antagonist composition of the present invention uses maltooligosaccharide having an NK1 receptor antagonistic activity as an active ingredient. A suitable amount of the maltooligosaccharide to be blended in the NK1 receptor antagonist composition of the present invention is 0.000001 to 70% by weight. The NK1 receptor antagonist composition of the present invention is prepared for use into various forms of external agents, internal medicines, foods and beverages by blending various materials as the ingredients other than the active ingredient. The NK1 receptor antagonist composition of the present invention has high safety for being used for pharmaceuticals and has satisfactory therapeutic effects.

7 Claims, No Drawings

OTHER PUBLICATIONS

Notice of Rejection issued Nov. 6, 2012 in Japanese Patent Application No. 2008-539786 (with English translation).
Office Action issued Jun. 26, 2012, in Japanese Patent Application No. 2008-539786 with English translation.
Kazutomo Imahori, et al., Dictionary of Biochemistry (seikagaku-jiten), Tokyo-Kagaku-dohjin Co., Ltd., Jul. 1, 2002, the fifth impression of the third edition, p. 258 with English translation.

* cited by examiner

```
                        SEQUENCE LISTING

<160> NUMBER OF SEQ ID NOS: 4

<210> SEQ ID NO 1
<211> LENGTH: 5
<212> TYPE: PRT
<213> ORGANISM: Unknown
<220> FEATURE:
<223> OTHER INFORMATION: Description of Unknown: Tachykinin mammalian
      peptide
<220> FEATURE:
<221> NAME/KEY: MOD_RES
<222> LOCATION: (2)..(2)
<223> OTHER INFORMATION: Any amino acid

<400> SEQUENCE: 1

Phe Xaa Gly Leu Met
1               5

<210> SEQ ID NO 2
<211> LENGTH: 11
<212> TYPE: PRT
<213> ORGANISM: Unknown
<220> FEATURE:
<223> OTHER INFORMATION: Description of Unknown: Substance P tachykinin
      mammalian peptide

<400> SEQUENCE: 2

Arg Pro Lys Pro Gln Gln Phe Phe Gly Leu Met
1               5                   10

<210> SEQ ID NO 3
<211> LENGTH: 10
<212> TYPE: PRT
<213> ORGANISM: Unknown
<220> FEATURE:
<223> OTHER INFORMATION: Description of Unknown: Neurokinin A tachykinin
      mammalian peptide
```

```
<400> SEQUENCE: 3

His Lys Thr Asp Ser Phe Val Gly Leu Met
1               5                   10

<210> SEQ ID NO 4
<211> LENGTH: 10
<212> TYPE: PRT
<213> ORGANISM: Unknown
<220> FEATURE:
<223> OTHER INFORMATION: Description of Unknown: Neurokinin B tachykinin
      mammalian peptide

<400> SEQUENCE: 4

Asp Met His Asp Phe Phe Val Gly Leu Met
1               5                   10
```

NK1 RECEPTOR ANTAGONIST COMPOSITION

TECHNICAL FIELD

The present invention relates to an NK1 receptor antagonist composition effective for treating or preventing symptoms and diseases mediated by an NK1 receptor.

BACKGROUND ART

As is well-known, peptides having a common structure (Phe-X-Gly-Leu-Met-NH2: SEQ ID NO:1) at a C terminus of their amino acid sequences are collectively referred to as tachykinin. Up to now, as tachykinin in mammals, three types, i.e., substance P (amino acid sequence: H-Arg-Pro-Lys-Pro-Gln-Gln-Phe-Phe-Gly-Leu-Met-NH2: SEQ ID NO:2), neurokinin A (amino acid sequence: H-His-Lys-Thr-Asp-Ser-Phe-Val-Gly-Leu-Met-NH2: SEQ ID NO:3) and neurokinin B (amino acid sequence: H-Asp-Met-His-Asp-Phe-Phe-Val-Gly-Leu-Met-NH2: SEQ ID NO:4) have been identified. These three tachykinins are neuropeptides commonly distributed in living organisms. Among these three tachykinins, physiological functions in substance P have been studied in most detail.

Substance P is the neuropeptide present in the living organisms of mammals and composed of 11 amino acid residues. This substance P has been known to be involved in various pathological conditions such as asthma, inflammation, pain, psoriasis, migraine, dyskinesia, cystitis, schizophrenia, emesis and anxiety, due to its localizations and functions (Non-patent Document 1).

The NK1 receptor has been identified as a receptor which exhibits a high affinity with substance P in the living organisms. That is, it has been found that substance P acts as an agonist which causes intracellular signal transduction by interacting with the NK1 receptor. Furthermore, there are antagonists which can antagonize or block binding between substance P which is such an agonist and the NK1 receptor. It has been also known that disorders, symptoms and diseases which can be ameliorated by such antagonists are widely ranged.

Examples of those conditions and diseases may include: respiratory diseases (such as cough, asthma, airway hypersensivity), cutaneous diseases (such as contact dermatitis, atopic dermatitis, inflammation, flare, urticaria, eczema and psoriasis), nervous inflammatory diseases (such as arthritis, migraine, nociception), CNS diseases (such as depression, manic disease, schizophrenia, stress-related disorder, obsessive-compulsive disorder, phobia, anxiety, alcohol dependency, psychoactive agent abuse, Parkinson's disease, dyskinesia, psychosis), eating disorders (e.g., hyperphagia, bulimia, anorexia nervosa, eating behavior disorder), pains (such as postoperative pain, chronic pain, neuropathic pain), pruritus, emesis, gastrointestinal disorder, renal disorder, urinary disorder, eyeball inflammation, allergic rhinitis, sleep disorder, premenstrual syndrome, obesity, headache, bladder disorder, urogenital disorder.

Various NK1 antagonists have been developed for the purpose of treating or preventing the symptoms and the diseases mediated by the NK1 receptor. For example, Non-patent Document 2 shows clinical trial examples that the NK1 receptor antagonist is effective for various diseases such as anxiety, depression, psychosis, schizophrenia and emesis. Also, Non-patent Document 3 shows clinical trial examples that the NK1 receptor antagonist is effective as an antiemetic drug.

Based on such findings, various NK1 receptor antagonists have been developed and reported. A majority of the reported NK1 receptor antagonists is a peptidic analog obtained by substituting a part of amino acid residues which compose substance P from the mammal with a D-amino acid residue(s) (see Non-patent Document 4 and Patent Document 1).

As mentioned above, the NK1 receptor antagonists developed until now are the peptides. No good pharmacodynamic nature is obtained from the peptide type NK1 receptor antagonist, which exerts only its limited activity in the living organisms. The peptide type NK1 receptor antagonist causes side effects due to its antigenicity to and agonistic action upon human bodies.

In response, it has been reported that a non-peptide type NK1 receptor antagonist is now under development (Non-patent Document 5, Patent Document 2).

Patent Document 1: U.S. Pat. No. 2,783,520
Patent Document 2: JP 2006-89499-A
Non-patent Document 1: Takayanagi, K., "Receptors on Cell Membrane" published by Nanzando, 1998
Non-patent Document 2: Kramer M S et al., Science 281 (5383), 1640-1645 (1998)
Non-patent Document 3: Gesztesi Z et al., Anesthesiology 93(4), 931-937 (2000)
Non-patent Document 4: Zubrzycka M et al., Endocrine Regulations, 34(1), 13-18 (2000)
Non-patent Document 5: Rost K et al., Med Monatsschr Pharm 29(6), 200-205 (2006)

DISCLOSURE OF INVENTION

Problem to be Solved by the Invention

As mentioned above, the majority of the NK1 receptor antagonists developed until now is developed by replacing a part of amino acid residues which is composed of the endogenous substance P derived from mammals with those such as the D-amino acid residue(s). These conventional NK1 receptor antagonists are the peptides; therefore, no good pharmacodynamic nature is obtained, which exerts only its limited activity in the living organisms. Also the conventional NK1 receptor antagonists cause side effects due to their antigenicity to and agonistic action upon the human bodies. Meanwhile, a non-peptide type NK1 receptor antagonist is currently under development. For example, several non-peptide type NK1 receptor antagonists (CP-96, 345) have been disclosed in R. M. Snider et al.: Science 251, 435-437 (1991). However, it has been reported, for example, in M. Caeser et al., Br. J.: Pharmacol. 109, 918-24 (1993) that while these NK1 receptor antagonists exhibit high selectivity for the NK1 receptor, they exhibit the remarkable affinity with several ionic channels, in particular an L type calcium channel because they have a quinuclidine ring. Therefore, it is concerned that the side effect on a cardiovascular system could be caused, thus the aforementioned non-peptide type NK1 receptor antagonist has not been in practical use. This way, under present circumstances, no NK1 receptor antagonist which is highly safe and have a satisfactory therapeutic effect has been still obtained.

The present invention has been made in the light of the above conventional circumstance, and an object thereof is to provide an NK1 receptor antagonist composition having the high safety for being used for pharmaceuticals and having a satisfactory therapeutic effect.

Means for Solving Problem

As a result of an extensive study for solving said problems, the present inventors have found that maltooligosaccharide has an excellent NK1 receptor antagonistic action. That is, it has been found that maltooligosaccharide is useful for treating or preventing symptoms and diseases involved with the NK1 receptor.

The present invention has been completed based on such a finding. That is, an NK1 receptor antagonist composition according to the present invention is characterized by containing the maltooligosaccharide having an NK1 receptor antagonistic activity as an active ingredient.

The maltooligosaccharide having the NK1 receptor antagonistic activity (hereinafter abbreviated as an NK1 antagonistic maltooligosaccharide) is disaccharide to nonasaccharide, preferably trisaccharide to hexasaccharide, and more preferably tetrasaccharide to pentasaccharide. Such maltooligosaccharide may specifically include maltose, maltotriose, maltotetraose, maltopentaose, maltohexaose and maltoheptaose. These maltooligosaccharides can be purchased from, for example, SIGMA.

A blending amount of the NK1 antagonistic maltooligosaccharide in the NK1 receptor antagonist composition according to the present invention is an effective amount. The blending amount of the NK1 antagonistic maltooligosaccharide, which is determined as the effective amount is appropriately selected depending on: a dose regimen of the NK1 receptor antagonist composition; a dosage form of the NK1 receptor antagonist composition; an age, a gender or other conditions of a subject; a symptom or a stage of a disease of a subject. Normally, it is fine to blend the amount of 0.000001 to 70% by weight, preferably 0.0001 to 35% by weight based on the total amount of the NK1 receptor antagonist composition. When the amount is less than 0.000001% by weight, the composition can not demonstrate the effects of the present invention. When it exceeds 70% by weight, the effects are not further enhanced and its production becomes difficult depending on its dosage form; thus, it is favorable that the blending amount does not exceed 70% by weight. A dosage is appropriately selected depending on the age, the gender, the other conditions, the symptom and the disease of the subject, and normally the dosage of 0.01 to 500 mg/kg/day is administered. A range of the dosage per day is preferably 0.01 to 100 mg/kg. For convenience, if desired, the total dosage per day may be divided and administered several times a day. In particular, when the composition is used as an external agent, it is normally fine to blend the amount of typically 0.000001 to 70% by weight, preferably 0.0001 to 35% by weight. When the amount is less than 0.000001% by weight, the composition can not demonstrate effects of the present invention. When it exceeds 70% by weight, the effects are not further enhanced, and the stability is not obtained, and additionally, its production becomes difficult depending on its dosage form; thus, it is favorable that the amount does not exceed 70% by weight.

The NK1 receptor antagonist composition of the present invention may be used not only as pharmaceuticals and quasi drugs such as external preparations, parenteral injections and internal medicines but also in forms of cosmetics, foods and beverages by appropriately selecting ingredients other than the NK1 antagonistic maltooligosaccharide which is the active ingredient.

When the NK1 receptor antagonist composition of the present invention is used as a skin topical composition, it is applied to the skin over the body and a scalp. For example, the composition can be prepared as external compositions and skin cosmetics such as creams, hand creams, milk lotions, face lotions, lotions, soaps, hand soaps, body soaps, bath agents, athlete's foot remedies, acne medications, anti-pruritic agents, eye drops and eye ointments; and as hair cosmetics such as shampoos, rinses, tonics and hair growth agents. In this case, as the ingredients other than the NK1 antagonistic maltooligosaccharide which is the active ingredient, the publicly known ingredients to be blended depending on types and dosage forms of the above skin topical agents, e.g., oils, water, surfactants, moisturizing agents, lower alcohols, thickeners, chelating agents, pigments, preservatives and perfumes may be appropriately blended in the NK1 receptor antagonist composition of the present invention. When the composition is used as an external agent for heads, ingredients other than the NK1 antagonistic maltooligosaccharide which is the active ingredient, for example, oil components, ultraviolet light absorbers, preservatives, moisturizing agents, surfactants, perfumes, water, alcohols, thickeners, color agents and drugs, may be blended.

When the NK1 receptor antagonist composition of the present invention is used as an internal agent, as the ingredients other than the NK1 antagonistic maltooligosaccharide which is the active ingredient, the publicly known ingredients to be blended; for example, excipients (e.g., lactose, saccharose, starch, mannitol), disintegrants (e.g., calcium carbonate, calcium carboxymethylcellulose), binders (e.g., pregelatinized starch, gum arabic, carboxymethylcellulose, polyvinyl pyrrolidone, hydroxypropylcellulose) or lubricants (e.g., talc, magnesium stearate, polyethylene glycol 6000) are first added, and then compressed and molded. Then, the internal medicine may be prepared by masking a taste and coating by a publicly known method for the purpose of imparting a durability, if necessary. As a coating agent, for example, ethylcellulose, hydroxymethylcellulose, polyoxyethylene glycol, cellulose acetate phthalate, hydroxypropylmethylcellulose phthalate and Eudragit (brand name: methacrylic acid-acrylic acid copolymer supplied from Rohm Pharma, Germany) may be used.

When the NK1 receptor antagonist composition of the present invention is used as a parenteral injection, as ingredients other than the NK1 antagonistic maltooligosaccharide which is the active ingredient, the publicly known ingredients to be blended, i.e., dispersing agents (e.g., Tween 80 [supplied from Atlas Powder Co., USA], HCO60 [supplied from Nikko Chemicals Co., Ltd.], polyethylene glycol, carboxymethylcellulose, sodium alginate), preservatives (e.g., methylparaben, propylparaben, benzyl alcohol, chlorobutanol, phenol), tonicity agents (e.g., sodium chloride, glycerine, sorbitol, glucose, invert sugar) are used. Then, the NK1 antagonistic maltooligosaccharide together with these other ingredients is dissolved, suspended or emulsified in an aqueous solvent (e.g., distilled water, saline, Ringer solution) or an oil solvent (e.g., vegetable oil such as olive oil, sesame oil, cottonseed oil or corn oil; and propylene glycol). By these steps, it is possible to produce the parenteral injection using the NK1 receptor antagonist composition. At that time, if desired, appropriately blend additives such as dissolution aids (e.g., sodium salicylate, sodium acetate), stabilizers (e.g., human serum albumin) and soothing agents (e.g., benzalkonium chloride, procaine hydrochloride) may appropriately be added.

When the NK1 receptor antagonist composition of the present invention is used as the foods, by blending various foodstuffs as the ingredients other than the NK1 antagonistic maltooligosaccharide which is the active ingredient, it is possible to prepare into forms of healthy foods, functional foods, foods for specified health use or foods for diseased patients.

When the NK1 receptor antagonist composition of the present invention is used as the beverages, by blending various materials for beverages as the ingredients other than the NK1 antagonistic maltooligosaccharide which is the active ingredient, it is possible to prepare into the forms of the beverages.

The NK1 receptor antagonist composition according to the present invention may be prepared into and used as foods ingested daily; and, the healthy foods and the functional foods ingested as supplements. By using the NK1 receptor antagonist composition for such foods and supplements, it is possible to continuously ingest the NK1 receptor antagonist composition. As a result, the function to prevent, reduce or solve the symptoms and the diseases mediated by the NK1 receptor can be realized in daily life particularly without being aware of its ingestion.

Various healthy foods and functional foods can be realized by selecting various foodstuffs as the ingredients other than the NK1 antagonistic maltooligosaccharide which is the active ingredient in the NK1 receptor antagonist composition of the present invention. In these healthy foods and functional foods, auxiliaries such as excipients, extenders, binders, disintegrants, lubricants, dispersing agents, preserving agents, moisturizing agents, dissolution aids, preservatives, stabilizers and capsule substrates in addition to food materials and food additives usually used may be used in the production of these healthy foods and functional foods. Specific example substances of these auxiliaries may include lactose, fructose, glucose, starch, gelatin, magnesium carbonate, synthetic magnesium silicate, talc, magnesium stearate, calcium carbonate, methylcellulose, carboxymethylcellulose, or salts thereof, gum arabic, polyethylene glycol, syrup, vaseline, glycerine, ethanol, propylene glycol, citric acid, sodium chloride, sulfite of soda, sodium phosphate, pullulan, carrageenan, dextrin, reduced palatinose, sorbitol, xylitol, stevia, synthetic sweeteners, citric acid, ascorbic acid, acidifiers, baking soda, sucrose esters, vegetable cured fats and oils, potassium chloride, safflower oil, bee waxes, soybean lecithin and perfumes. Concerning the production of such healthy foods and functional foods, it is possible to refer to reference books for pharmaceutical preparations, e.g., "Commentary to the Japanese Pharmacopoeia (preparation general rules)" (Hirokawa Shoten).

As shapes suitable for the healthy foods and the functional foods, tablets, capsules, granules, powders, suspensions and emulsification may be exemplified. For specifically producing the tablet healthy food and functional food, the NK1 receptor antagonist composition of the present invention is prepared into each food form which is then compressed to make a certain shape, or alternatively a kneaded one obtained by wetting the NK1 receptor antagonist composition of the present invention with a solvent such as water or alcohol is made into the certain shape or is poured and molded in a certain mold. Specific examples for producing capsules of the healthy food and the functional food are shown as follows: a blend obtained by preparing the NK1 receptor antagonist composition of the present invention is filled in the capsule in a liquid, suspension, glue, powder or granular form; or alternatively the NK1 receptor antagonist composition of the present invention is encapsulated with a capsule substrate, thus producing hard capsules and soft capsules.

Specific examples of the foods which can be prepared from the NK1 receptor antagonist composition of the present invention may include, but are not limited to, breads and confectioneries such as western confectioneries, e.g., purine, cookies, crackers, potato chips, biscuits, breads, cakes, chocolates, doughnuts and jerry, and Japanese confectioneries, e.g., rice crackers, sweet jelly of beans, rice cake stuffed with bean jam, rice dumpling covered with bean jam, other steamed bean-jam buns and castella, frozen dessert (candies etc.) and chewing gums; noodles such as Japanese white noodles, buckwheat noodles and Japanese flat noodles; fish cakes such as steamed fish pastes, hams and fish sausages; meat products such as hams, sausages, hamburgers, salt beef; seasonings such as salts, peppers, soybean pastes, soybean sauces, sauces, dressings, mayonnaise, ketchup, sweeteners and hot spices; foods roasted on a hotplate such as Akashi-yaki, octopus dumpling, Monja-yaki, Japanese style pancake containing vegetables and other foodstuffs, pan-fried noodles and fried white noodles; milk products such as cheeses and hard-type yoghurt; various prepared foods such as fermented soybeans, deep-fried soybean curd, soybean curd, alimentary yam paste, rice dumplings, pickles, fish boiled in soy sauce, steam-baked meat pie, steamed meatball dumplings, croquette, sandwiches, pizza, hamburgers and salads; various powders (stock farm products such as beef, pork and chicken, marine products such as shrimps, scallop, fresh-water clam and seaweeds, vegetables, fruits, plants, yeast, algae), powdered and solidified ones of fats and oils and perfumes (vanilla, citrus, bonito), and powdered beverage products (instant coffee, instant tea, instant milk, instant soup, soybean paste soup).

The NK1 receptor antagonist composition of the present invention can be ingested continuously everyday if used in the beverage form. The beverage is the product drunk continuously. Therefore, the beverage using the NK1 receptor antagonist composition can simultaneously have the function to prevent, reduce or solve the symptoms and the diseases mediated by the NK1 receptor, in addition to its original function to quench thirst.

The types of the beverages prepared from the NK1 receptor antagonist composition of the present invention may include those having various compositions. When those beverages are produced, any of sugars, perfumes, fruit juices and food additives, which are commonly used for formulating and designing the beverages, may be employed. Concerning the production of the beverage, it is possible to refer to the existing reference books, e.g., "Revised New Version Soft Drinks" (Korin Publishing Co., Ltd.).

When the NK1 receptor antagonist composition of the present invention is made into the form of the beverage, specific examples of beverage materials blended as the ingredients other than the NK1 antagonistic maltooligosaccharide which is the active ingredient may include various beverage materials such as drink types of yoghurt, fruit juices of apples, mandarin oranges, grapes, bananas, pears, Japanese apricots and water melons, vegetable juices of tomatoes, carrots, celeries and cucumbers, cooling beverages, cow milk, soybean milk, coffee, cocoa, black tea, green tea, barley tea, brown rice tea, natural leaf tea, refined green tea(gyokuro), roasted green tea, oolong tea, various herb teas such as turmeric tea, Puer tea, Rooibos tea, rose tea, chrysanthemum tea, mint tea and jasmine tea, sport drinks, mineral water and nutrition supplement drinks.

Effect of the Invention

The NK1 receptor antagonist composition of the present invention is useful for preventing and treating various symptoms or diseases mediated by the NK1 receptor (e.g., pruritus, pain, emesis, cough, asthma, dermatitis such as atopic dermatitis, contact dermatitis and urticaria, depression, alopecia) because the NK1 antagonistic maltooligosaccharide which is its active ingredient has the NK1 receptor antagonistic activity. It is obvious that the NK1 receptor antagonist composition of the present invention is highly safe and scarcely has the side effect because the maltooligosaccharide as an active ingredient is contained in foods.

BEST MODES FOR CARRYING OUT THE INVENTION

Examples of the present invention will be described below. The Examples shown below are only exemplifications for suitably explaining the present invention, and do not limit the present invention at all.

EXAMPLES

Example 1

In this Example 1, it was confirmed that the NK1 antagonistic maltooligosaccharide which is the active ingredient of the NK1 receptor antagonist composition of the present invention antagonized substance P signaling in the prevention or treatment of various symptoms or diseases mediated by the NK1 receptor (e.g., pruritus; pain; emesis; cough; asthma; dermatitis such as atopic dermatitis, contact dermatitis and urticaria; depression; and alopecia). This activity was confirmed by the following assay.

[Performance Evaluation Test] NK1 Receptor Antagonism Assay (Preparation of Reagents)

In this test, maltose, maltotriose, maltotetraose, maltopentaose, maltohexaose and maltoheptaose were purchased from SIGMA, isomaltose, isomaltotriose, isomaltotetraose, isomaltopentaose, isomaltohexaose and isomaltoheptaose were purchased from Seikagaku Corporation, and four types of oligosaccharides-1-kestose, fructofranosylnystose, nystose and galactotetraose—were purchased from Wako Pure Chemicals Industries Ltd. Each oligosaccharide was diluted with saline, and used.

(Cloning cDNA Encoding Human NK1 Receptor and Preparation of Expression Vector Expressed in Animal Cells)

In order to transiently express a cloned human NK1 receptor in HEK293, cDNA of the human NK1 receptor was cut out from pCDM8 (Invitrogen), and cloned in an expression vector pCDM9 derived by inserting an ampicillin resistant gene (BLUESCRIPT, nucleotides 1973 to 2964 from SK+) at a SacII site.

(Preparation of Human NK1 Receptor-Expressing HEK293)

HEK293 cells were seeded at $1 \times 10^5$ cells in a Falcon dish (diameter: 3.5 cm) using α-MEM medium (Gibco) containing 10% bovine fetal serum, and cultured in a 5% $CO_2$ incubator at 37° C. overnight. Then, 20 μg of the expression vector was transfected using Transfection Reagent FuGENE6 (Roche) according to attached instructions, and the transfectants were incubated at 37° C. for 3 days and assayed by a calcium imaging method.

(Preparation of NK1 Receptor-Expressing Nerve Cells)

According to Renganathan et al's method (Renganathan M et al., J. Neurophysiol., 84(2), 710-82 (2000)), nerve cells were dispersed and isolated from spinal dorsal root ganglion in a wild type mouse, and $1 \times 10^5$ thereof were seeded in a 24-well plate coated with poly-L-lysine. The cells were cultured in 90% DMEM medium (GIBCO) supplemented with 10% bovine fetal serum, 2 mM glutamine, 100 U/mL of penicillin/streptomycin, 100 ng/mL of NGF (SIGMA) and 5 μM cytosine arabinoside (SIGMA) under 5% $CO_2$ at 37° C. The cells were cultured for 1 to 3 weeks, and subsequently subjected to a calcium imaging analysis. A half of the nerve cells was identified to be positive for the NK1 receptor by staining the nerve cells derived from spinal dorsal root ganglion in the wild type mouse with an anti-NK1 receptor antibody (supplied from CHEMICON International).

(Calcium Imaging Measurement Method)

The cells which express the NK1 receptor transiently or constitutively were subjected to measurement using a high resolution digital B/W cooling CCD camera (ORCA supplied from Hamamatsu Photonics K.K.), and their images were analyzed using an analysis software (AQUA COSMOS supplied from Hamamatsu Photonics K.K.). When the cells were labeled for calcium, Fluo4-AM (supplied from Molecular Probe) was used as a calcium sensitive dye. Fifty μg of Fluo4-AM was dissolved in 400 μL of DMSO in a vial, 4 μL of Pluronic F-127 (Molecular Probe) was added and mixed, and then 4 mL of OPTI-MEM (GIBCO) was added thereto. The calcium sensitive dye solution thus prepared was added to the cells, which were then incubated at 37° C. for 60 minutes. An agonist, an antagonist and samples to be evaluated were prepared at concentrations which were 10 times higher than assay concentrations, and analyzed by adding a one tenth volume of the cell suspension upon analysis. All reagents and an assay temperature were kept at 37° C. For the cells transfected transiently, YFP reporter DNA fluorescence (excitation: 490 nm) was used for identifying the transfected cells. Upon measurement, a fluorescence intensity obtained by initially imaging the untreated cells was made an initial value. After passing one minute, a change of calcium/fluorescence intensity in the sample to be evaluated at the desired concentration was monitored with an interval of one second before and after the addition (2 to 5 minutes). Subsequently, substance P was added, and immediately after (2 to 5 minutes), an antagonistic activity of the sample to be evaluated was determined by monitoring the change of intracellular calcium concentrations as the change of the fluorescence intensities with the interval of one second.

(Calculation Method of NK1 Receptor Antagonistic Activity)

The NK1 receptor antagonistic activity in the sample to be evaluated was calculated according the following formula (1). Fifteen cells which expressed the NK1 receptor were selected per one measurement, and change of the fluorescence intensity was recorded for each cell. Antagonistic activity values of all measured cells were averaged based on the antagonistic activity regarding each cell obtained by the following formula (1); thus, the antagonistic activity value of the sample to be evaluated was worked out.

Mathematical formula 1

$$\text{Antagonistic Activity of Samples to be evaluated} = \left(1 - \frac{C-A}{B-A}\right) \times 100(\%) \quad (1)$$

In the formula (1), A, B and C mean the following values.

A: Initial fluorescence intensity in the cell before adding the sample.

B: Maximum fluorescence intensity in the cell after adding substance P (100 μM).

C: Maximum fluorescence intensity in the cell pretreated with the sample and then treated with substance P (100 μM).

(Evaluation Criteria for Efficacy of Sample to be Evaluated)

The efficacy of the sample to be evaluated was determined by comparing the antagonistic activity of the sample with the antagonistic activity of a standard substance SPANTIDE II (peptidic analog of substance P).

The evaluation criteria was given as follows.

The efficacy was determined on four levels (A, B, C and D) based on the antagonistic activity of SPANTIDE II as a positive control. Results are shown in Table 1. The NK1 receptor antagonistic activity of SPANTIDE II was 65%.

A: Complete response: the antagonistic activity was 75% or more and much more excellent performance than in the positive control was shown.

B: Effective: the antagonistic activity was 65% or more and less than 75% and the more excellent performance than in the positive control was shown.

C: Slightly effective: the antagonistic activity was less than 65%, and a stimulating or agonistic activity of the sample was weak.

D: Ineffective: the antagonistic activity was less than 65%, or the stimulating or agonistic activity of the sample was strong.

TABLE 1

(Table 1) Results of efficacy evaluation of samples to be evaluated

| Samples to be evaluated | Evaluated concentration | Efficacy |
|---|---|---|
| SPANTIDE II | 100 ppm | — |
| 1-Kestose | 1000 ppm | D |
| Fructofranosylnystose | 1000 ppm | D |
| Nystose | 1000 ppm | D |
| Galactotetraose | 1000 ppm | D |
| Isomaltose | 1000 ppm | D |
| Isomaltotriose | 1000 ppm | D |
| Isomaltotetraose | 1000 ppm | D |
| Isomaltopentaose | 1000 ppm | D |
| Isomaltohexaose | 1000 ppm | D |
| Isomaltoheptaose | 1000 ppm | D |
| Maltose | 1,000 ppm | B |
|  | 100 ppm | C |
|  | 10 ppm | C |
|  | 1 ppm | D |
|  | 0.1 ppm | D |
| Maltotriose | 1,000 ppm | A |
|  | 100 ppm | B |
|  | 10 ppm | C |
|  | 1 ppm | C |
|  | 0.1 ppm | C |
| Maltotetraose | 1,000 ppm | A |
|  | 100 ppm | A |
|  | 10 ppm | A |
|  | 1 ppm | A |
|  | 0.1 ppm | B |
| Maltopentaose | 1,000 ppm | A |
|  | 100 ppm | A |
|  | 10 ppm | B |
|  | 1 ppm | B |
|  | 0.1 ppm | B |
| Maltohexaose | 1,000 ppm | B |
|  | 100 ppm | B |
|  | 10 ppm | B |
|  | 1 ppm | C |
|  | 0.1 ppm | C |
| Maltoheptaose | 1,000 ppm | B |
|  | 100 ppm | B |
|  | 10 ppm | C |
|  | 1 ppm | C |
|  | 0.1 ppm | D |

As is evident from Table 1, the high effect as the NK1 receptor antagonist was observed in maltose, maltotriose, maltotetraose, maltopentaose, maltohexaose and maltoheptaose, which were maltooligosaccharides. In particular, maltotetraose and maltopentaose exhibited the high efficacy at a low concentration which was 0.1 ppm, and the efficacy of maltotriose, maltohexaose, maltoheptaose and maltose followed thereto. Meanwhile, no NK1 receptor antagonistic activity was observed at all in isomaltose, isomaltotriose, isomaltotetraose, isomaltopentaose, isomaltohexaose, isomaltoheptaose, 1-kestose, fructofranosylnystose, nystose and galactotetraose used as the other oligosaccharides for the evaluation. From the results in this Example 1, it has been confirmed that the maltooligosaccharide is less stimulatory and has the performance which is very specific and excellent as the NK1 receptor antagonist.

Examples 2 to 5 and Comparative Examples 1 to 3

Blending examples for the NK1 receptor antagonist composition of the present invention specializing to skin topical agents are shown below (Table 2). In Comparative Examples 1 to 3 corresponding to these Examples, no maltooligosaccharide was added and the other oligosaccharides were added. The blended ingredients other than the oligosaccharide are the same in the following Examples 2 to 5 and Comparative Examples 1 to 3.

TABLE 2

(Table 2) (Skin topical agents)

| Ingredient | Example 2 | Example 3 | Example 4 | Example 5 | Comparative Example 1 | Comparative Example 2 | Comparative Example 3 |
|---|---|---|---|---|---|---|---|
| Maltotriose | 1.00 | — | — | — | — | — | — |
| Maltotetraose | — | 1.00 | — | — | — | — | — |
| Maltopentaose | — | — | 1.00 | — | — | — | — |
| Maltohexaose | — | — | — | 1.00 | — | — | — |
| Isomaltotetraose | — | — | — | — | 1.00 | — | — |
| Isomaltopentaose | — | — | — | — | — | 1.00 | — |
| Liquid paraffin | 5.00 | 5.00 | 5.00 | 5.00 | 5.00 | 5.00 | 5.00 |
| Paraffin | 3.00 | 3.00 | 3.00 | 3.00 | 3.00 | 3.00 | 3.00 |
| Dimethyl silicon | 2.00 | 2.00 | 2.00 | 2.00 | 2.00 | 2.00 | 2.00 |
| Cetyl palmitate | 2.00 | 2.00 | 2.00 | 2.00 | 2.00 | 2.00 | 2.00 |
| Cetostearyl alcohol | 4.00 | 4.00 | 4.00 | 4.00 | 4.00 | 4.00 | 4.00 |

TABLE 2-continued (Table 2) (Skin topical agents)

| Ingredient | Example 2 | Example 3 | Example 4 | Example 5 | Comparative Example 1 | Comparative Example 2 | Comparative Example 3 |
|---|---|---|---|---|---|---|---|
| Olive oil | 2.00 | 2.00 | 2.00 | 2.00 | 2.00 | 2.00 | 2.00 |
| Jojoba oil | 2.00 | 2.00 | 2.00 | 2.00 | 2.00 | 2.00 | 2.00 |
| Glyceryl monostearate | 1.50 | 1.50 | 1.50 | 1.50 | 1.50 | 1.50 | 1.50 |
| POE cured castor oil | 3.00 | 3.00 | 3.00 | 3.00 | 3.00 | 3.00 | 3.00 |
| Hydrogenated lecithin | 2.00 | 2.00 | 2.00 | 2.00 | 2.00 | 2.00 | 2.00 |
| 1,3-Butylene glycol | 5.00 | 5.00 | 5.00 | 5.00 | 5.00 | 5.00 | 5.00 |
| p-Hydroxycinnamic acid 2-ethylhexyl | 0.10 | 0.10 | 0.10 | 0.10 | 0.10 | 0.10 | 0.10 |
| 4-tert-Butyl-4'-methoxy-dibenzoylmethane | 0.25 | 0.25 | 0.25 | 0.25 | 0.25 | 0.25 | 0.25 |
| Carboxyvinyl polymer | 0.05 | 0.05 | 0.05 | 0.05 | 0.05 | 0.05 | 0.05 |
| Xanthan gum | 0.10 | 0.10 | 0.10 | 0.10 | 0.10 | 0.10 | 0.10 |
| Triisopropanolamine | 0.10 | 0.10 | 0.10 | 0.10 | 0.10 | 0.10 | 0.10 |
| Citric acid/sodium citrate | Adequate dose [*1] | Adequate dose [*1] | Adequate dose [*1] | Adequate dose [*1] | Adequate dose [*1] | Adequate dose [*1] | Adequate dose [*1] |
| Methylparaben | 0.30 | 0.30 | 0.30 | 0.30 | 0.30 | 0.30 | 0.30 |
| Perfume | 0.05 | 0.05 | 0.05 | 0.05 | 0.05 | 0.05 | 0.05 |
| Purified water | Remainder | Remainder | Remainder | Remainder | Remainder | Remainder | Remainder |
| Antipruritic effect | B | A | A | B | D | D | D |

[*1] Citric acid and sodium citrate are pH adjusters and the adequate dose is an amount required for adjusting pH to 3.5. A unit in Table is % by mass.

(Evaluation of Antipruritic Property)

To six persons (2 males and 4 females) having the chronic pruritus, 0.5 g of the skin topical agent shown in Examples 2 to 5 (Table 2) was applied once to a site where they felt pruritus. Likewise, 0.5 g of the skin topical agent in Comparative Examples 1 to 3 was applied once to the site where they felt pruritus. Each skin topical agent was applied so that each evaluation day was shifted each other. By applying so that the evaluation day was shifted, the antipruritic property was evaluated. A sensory evaluation (3: complete response, 2: effective, 1: yes and no, 0: ineffective) for suppression of pruritus was performed 30 minutes after the application, average scores of the 6 persons were calculated, and the antipruritic effect was determined according to the following criteria. The results were shown together in Table 2.

(Determination Criteria for Antipruritic Effect)
D: An average score was 0 or more and less than 0.7.
C: The average score was 0.7 or more and less than 1.5.
B: The average score was 1.5 or more and less than 2.4.
A: The average score was 2.4 or more and 3.0 or less.

Example 6

A blending Example for the NK1 receptor antagonist composition of the present invention specializing to an internal liquid agent is shown in Table 3. A total volume of each internal liquid agent was 30 mL. As Comparative Example 4 corresponding to this Example 6, an internal liquid agent was prepared by blending the same ingredients as in Example 6, except that no oligosaccharide was added.

TABLE 3

(Table 3) (Internal liquid medicine)

| Ingredient names | Example 6 Blended amount (mg/bottle (30 mL)) | Comparative Example 4 Blended amount (mg/bottle (30 mL)) |
|---|---|---|
| Maltotetraose | 1 | — |
| Sodium ascorbate | 535 | 535 |
| Sodium phosphate ripoflavin | 12 | 12 |
| Pyridoxine hydrochloride | 10 | 10 |
| Purified saccharose | 3000 | 3000 |
| Propylene glycol | 2000 | 2000 |
| Polysorbate 80 | 50 | 50 |
| Sodium benzoate | 20 | 20 |
| Ethyl paraoxybenzoate | 3.5 | 3.5 |
| Perfume (derived from citrus) | Trace amount [*1] | Trace amount [*1] |
| Purified water | Remainder | Remainder |
| Antipruritic effect | B | D |

[*1] The trace amount is the amount in the range of 0.1% (mass percentage) or less based on the total amount.

(Evaluation of Antipruritic Property)

Six persons (2 males and 4 females) having the chronic pruritus were divided into two groups of three persons (1 male and 2 females). One bottle of the internal liquid agent of Example 6 was ingested by the group I and the antipruritic effect was evaluated. The sensory evaluation (3: complete response, 2: effective, 1: yes and no, 0: ineffective) for the suppression of pruritus was performed one hour after the ingestion. After a week, one bottle of the internal liquid medicine of Comparative Example 4 was ingested and the antipruritic effect was evaluated. Likewise, the sensory test was performed. In another group, the internal liquid medicine of Comparative Example 4 was ingested in advance and after a week, the internal liquid medicine of Example 6 was ingested, and the same evaluation was performed. The average scores of the 6 persons were calculated, and the antipruritic effect was determined according to the following criteria. The results were shown together in Table 3.

(Determination Criteria for Antipruritic Effect)
D: The average score was 0 or more and less than 0.7.
C: The average score was 0.7 or more and less than 1.5.
B: The average score was 1.5 or more and less than 2.4.
A: The average score was 2.4 or more and 3.0 or less.

Example 7

The NK1 receptor antagonist composition of the present invention was processed into a tablet agent, and its effect was confirmed. Blending Examples and evaluation results are shown in Table 4. The total amount of each tablet agent was 300 mg. As Comparative Example 5 corresponding to this Example 7, a tablet agent was prepared by blending the same ingredients as in Example 7, except that no oligosaccharide was added.

(Evaluation of Antipruritic Property)

Six persons (2 males and 4 females) having the chronic pruritus were divided into two groups of three persons (1 male and 2 females). One tablet of the tablet agent of Example 7 was ingested by the group I and the antipruritic effect was evaluated. The sensory evaluation (3: complete response, 2: effective, 1: yes and no, 0: ineffective) for the suppression of pruritus was performed one hour after the ingestion. After a week, one tablet of the tablet agent of Comparative Example 5 was ingested by the same subjects and the antipruritic effect was evaluated. Likewise, the sensory test was performed. In another group, the tablet agent of Comparative Example 5 was ingested in advance and after a week, the tablet agent of Example 7 was ingested, and the same evaluation was performed. The average scores of the 6 persons were calculated, and the antipruritic effect was determined according to the following criteria. The results were shown together in Table 4.

(Determination Criteria for Antipruritic Effect)
D: The average score was 0 or more and less than 0.7.
C: The average score was 0.7 or more and less than 1.5.
B: The average score was 1.5 or more and less than 2.4.
A: The average score was 2.4 or more and 3.0 or less.

TABLE 4

| | | |
|---|---|---|
| | (Table 4) (Tablet agents) | |
| Ingredient names | Example 7 Blended amount (mg/Tablet (300 mg)) | Comparative Example 5 Blended amount (mg/Tablet (300 mg)) |
| Maltotetraose | 5 | — |
| Hydrated crystalline glucose | 150 | 155 |
| Crystalline cellulose | 70 | 70 |
| Egg shell calcium | 45 | 45 |
| Sucrose fatty acid ester | 30 | 30 |
| Antipruritic effect | B | D |

A blending Example of the other dosage form using the NK1 receptor antagonist composition is shown below.

TABLE 5

(Table 5) (Blending Example 1) (Cream)

| Composition | % by mass |
|---|---|
| (Internal aqueous phase) | |
| Maltotetraose | 1.0 |
| 1,3-Butylene glycol | 1.5 |
| Purified water | 32.5 |
| (Oil phase) | |
| Squalane | 6.5 |
| Olive oil | 2.5 |
| Stearic acid | 0.5 |
| Cetanol | 0.9 |
| Sorbitan monooleate | 4.5 |
| Propylparaben | 0.1 |
| (External aqueous phase) | |
| Diisopropanolamine | 0.02 |
| Monostearic acid PEG | 1.0 |
| Purified water | 48.98 |
| Total | 100.0 |

(Preparation Method)

An internal aqueous phase, an oil phase and an external aqueous phase were each separately stirred and dissolved uniformly at 60 to 70° C. The internal aqueous phase was slowly added to the oil phase with stirring at high speed (4000 to 5000 rpm) using a homomixer under the condition at 60 to 70° C. to yield a W/O type emulsion. Subsequently, as the external aqueous phase was stirred (500 to 600 rpm) using Three One Motor under the condition at 50 to 60° C., the W/O type emulsion previously prepared was added thereto and the mixture was emulsified for 40 to 50 minutes to yield a external agent composition containing a W/O/W type complex emulsion having the above composition (production rate: 85%). This composition had a good availability and was stable at 40° C. for two months.

TABLE 6

(Table 6) (Blending Example 2) (Hair growth agent)

| Composition | % by mass |
|---|---|
| Maltotetraose | 1.0 |
| Triethylhexyl citrate | 5.0 |
| Monooctanoic acid propylene glycol | 1.0 |
| Ethyl oleate | 2.0 |
| Polyethylene glycol 400 | 1.0 |
| Monopentadecanoic acid glyceride | 3.0 |
| Glycerine | 1.0 |
| Palm oil fatty acid sorbitan | 1.0 |
| Sucrose myristate ester | 1.0 |
| Decaglyceryl myristate | 1.0 |
| Lauryldimethylaminoacetic acid betaine | 0.5 |
| Ampholytic polymer[*1] | 0.2 |
| Succinic acid | 0.1 |
| Perfume[*2] | 0.5 |
| Purified water | 0.3 |
| 99% Ethanol | Remainder |
| Total | 100.0 |

[*1]N-methacroyloxyethyl-N,N-dimethylammonium•α-N-methylcarboxybetaine alkyl methacrylate copolymer

[*2]Perfume composition A disclosed in JP 2003-113019-A (Tables 2 to 25).

TABLE 7

(Table 7) (Blending Example 3) (Hair growth spray)

| Composition | % by mass |
|---|---|
| Maltotetraose | 1.0 |
| Octyldodecyl lactate | 2.0 |
| Polyethylene glycol 300 | 0.5 |
| Isopropyl myristate | 2.0 |
| Monopentadecanoic acid glyceride | 2.0 |
| Isopropylmethylphenol | 0.5 |
| Ampholytic polymer*[1] | 0.2 |
| Succinic acid | 0.3 |
| Sucrose myristate ester | 0.5 |
| Sorbitan monolaurate | 0.5 |
| Decaglyceryl myristate | 0.5 |
| Glycerine | 00.5 |
| 1-Menthol (synthesized) | 0.3 |
| Purified water | 0.3 |
| Perfume*[3] | 0.5 |
| 99% Ethanol | Remainder |
| Total | 100.0 |

TABLE 7-continued (Table 7) (Blending Example 3) (Hair growth spray)

| Composition | % by mass |
|---|---|
| (Filler for dilution) | |
| Above original solution | 71.0 |
| Dimethyl ether | 30.0 |
| Total | 100.0 |

*[1] N-methacroyloxyethyl-N,N-dimethylammonium•α-N-methylcarboxybetaine alkyl methacrylate copolymer
*[3] Perfume composition C disclosed in JP 2003-113019-A (Tables 2 to 25).

INDUSTRIAL APPLICABILITY

As described above, the NK1 receptor antagonist composition according to the present invention has the maltooligosaccharide which has the good NK1 antagonism and is highly safe for living organisms as an active ingredient. Therefore, the NK1 receptor antagonist composition according to the present invention is effective for treating the symptoms and the diseases mediated by the NK1 receptor. The NK1 receptor antagonist composition according to the present invention can be easily prepared into the various forms of external agents, internal medicines, foods and beverages by blending various materials as ingredients other than the active ingredient, and thus, digested daily and easily.

The invention claimed is:

1. A method for treating or reducing the severity of pruritus comprising: administering to the skin of a subject suffering from pruritus an effective amount of a composition comprising a maltooligosaccharide selected from the group consisting of maltotriose, maltotetraose, maltopentaose, maltohexaose, and any combination thereof; wherein said maltooligosaccharide is in the range from 0.00001% by weight to 70% by weight of said composition; wherein said method reduces the severity of pruritus to a greater extent that an otherwise identical method of administering an otherwise identical composition that does not contain maltotriose, maltotetraose, maltopentaose, maltohexaose, and any combination thereof.

2. The method according to claim 1, which comprises administering an amount of said maltooligosaccharide effective to antagonize the interaction between NK1 and an agonist for NK1.

3. The method according to claim 1, wherein said maltooligosaccharide is maltotetraose and/or maltopentaose.

4. The method according to claim 1, wherein the maltooligosaccharide is maltotriose.

5. The method according to claim 1, wherein the maltooligosaccharide is maltotetraose.

6. The method according to claim 1, wherein the maltooligosaccharide is maltopentaose.

7. The method according to claim 1, wherein the maltooligosaccharide is maltohexaose.

* * * * *